United States Patent [19]  [11] 4,174,337
Birkmeyer et al.  [45] Nov. 13, 1979

[54] HYDROXY-FUNCTIONAL ESTERS OF SUBSTITUTED IMIDAZOLIDINEDIONES AND COMPOSITIONS CONTAINING SAME

[75] Inventors: William J. Birkmeyer, Oakmont; J. Alden Erikson, Gibsonia; Ronald J. Lewarchik, Natrona Heights, all of Pa.

[73] Assignee: PPG Industries, Inc., Pittsburgh, Pa.

[21] Appl. No.: 950,096

[22] Filed: Oct. 10, 1978

[51] Int. Cl.$^2$ .............................................. C08K 5/06
[52] U.S. Cl. ................................ 260/31.4 R; 528/73; 528/367; 548/310
[58] Field of Search ................ 548/310, 312; 526/263; 528/73, 367, 407, 418; 260/31.4 R

[56] References Cited

U.S. PATENT DOCUMENTS

| | | | |
|---|---|---|---|
| 3,629,263 | 12/1971 | Batzer | 548/312 |
| 3,631,221 | 12/1971 | Batzer | 548/312 |
| 3,808,226 | 4/1974 | Habermeier | 548/312 |
| 3,813,352 | 5/1974 | Habermeier | 260/2 EP |
| 3,852,302 | 12/1974 | Habermeier | 548/312 |
| 4,100,348 | 7/1978 | Habermeier | 528/73 |

*Primary Examiner*—Paul R. Michl
*Attorney, Agent, or Firm*—Charles R. Wilson

[57] ABSTRACT

Hydroxy-functional esters of substituted imidazolidinediones have the formula:

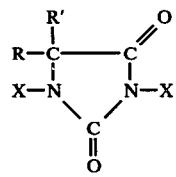

where X is hydrogen,

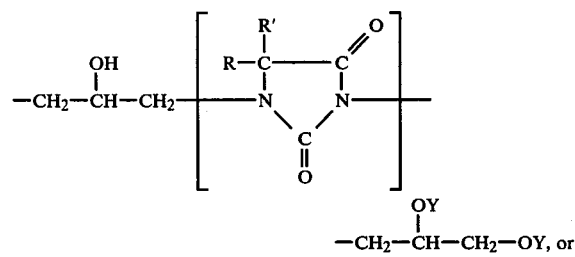

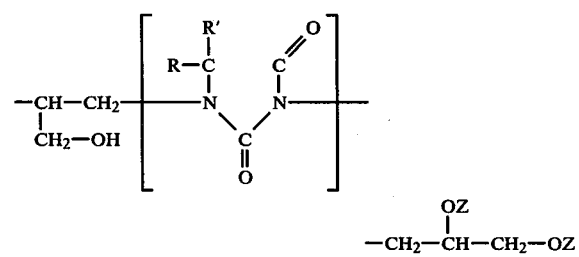

provided both X's are not hydrogen, where R and R' are independently hydrogen or hydrocarbon groups having 1 to 8 carbon atoms, with one Y being hydrogen, one Z being hydrogen and the other Y and Z being

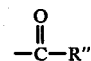

where the R" groups are independently hydrocarbon groups having from 1 to 17 carbon atoms. The novel compounds are especially useful when formulated with a crosslinking agent and used in low organic solvent-containing coating compositions.

34 Claims, No Drawings

HYDROXY-FUNCTIONAL ESTERS OF SUBSTITUTED IMIDAZOLIDINEDIONES AND COMPOSITIONS CONTAINING SAME

BACKGROUND OF THE INVENTION

The subject invention relates to novel esters and coating compositions containing them. More particularly, it relates to hydroxy-functional esters of substituted imidazolidinediones and their use in coating compositions.

There have been recent concerns as to the polluting effects and health concerns associated with the use of organic solvents. Many useful coating compositions contain appreciable amounts of organic solvents. Precautions in the use of the coating compositions and the installation of solvent recovery systems have alleviated some of the concerns. However, it would still be desirable to formulate coating compositions containing little or no organic solvent.

Various attempts have been made to lower the organic solvent content in coating compositions. One line of work has concentrated on using water as the liquid carrier in place of the organic solvent. However, this has necessitated changes in the resin formulations with a consequent change in performance obtained from the coating compositions.

Another line of work has attempted to formulate coating compositions containing a high solids content, and thus low organic solvent content. The problem associated with many of the high solids coating compositions has been the fact such compositions normally are highly viscous and are hard to apply using conventional coating techniques. The formulation of coating compositions having a low organic solvent content which also possess a viscosity which allows the composition to be applied by conventional techniques would be most desirable.

There have now been found novel compounds which when properly formulated into coating compositions provide compositions which can be readily applied and give coatings having a desired set of properties.

As used herein, all percents and ratios are by weight unless otherwise indicated.

SUMMARY OF THE INVENTION

The esters described herein have the formula:

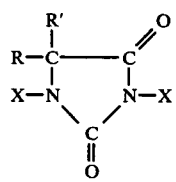

where X is hydrogen,

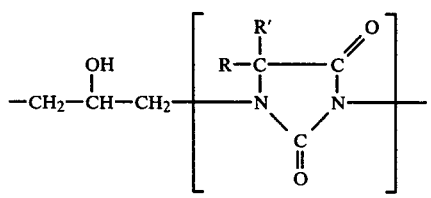

-continued $-CH_2-CH(OY)-CH_2-OY$, or

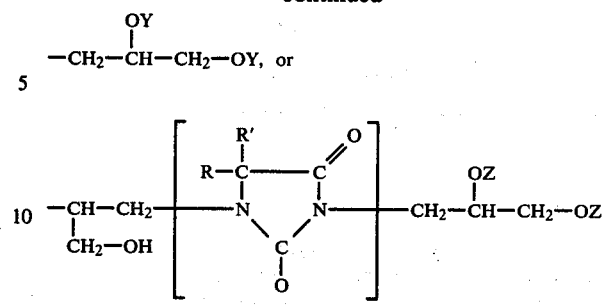

provided both X's are not hydrogen, where R and R' are independently hydrogen or hydrocarbon groups having 1 to 8 carbon atoms, with one Y being hydrogen, one Z being hydrogen and the other Y and Z being

where the R'' groups are independently hydrocarbon groups having from 1 to 17 carbon atoms.

The above hydroxy-functional esters of substituted imidazolidinediones are especially useful when formulated with a crosslinking agent selected from the group consisting of aminoplasts, isocyanates, blocked isocyanates, phenoplasts, and mixtures thereof to form a coating composition. The coating compositions can have an organic solvent content of below about 40 percent.

DETAILED DESCRIPTION OF THE INVENTION

The following paragraphs describe the hydroxy-functional esters of substituted imidazolidinediones, their process of making and their use in coating compositions.

Hydroxy-functional esters of substituted imidazolidinediones of this invention have the structure:

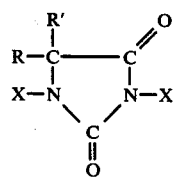

where X is hydrogen,

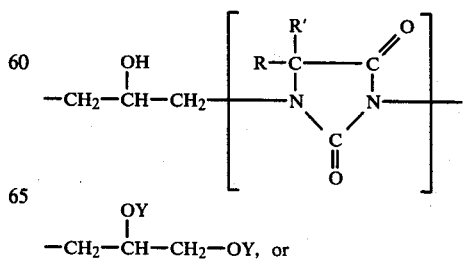

$-CH_2-CH(OY)-CH_2-OY$, or

-continued

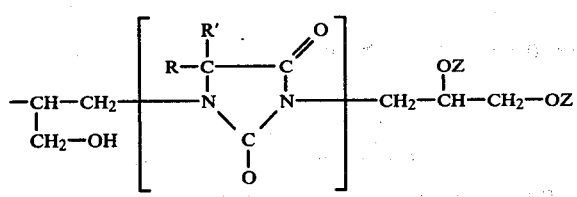

provided both X's are not hydrogen, where R and R' are independently hydrogen or hydrocarbon groups having 1 to 8 carbon atoms, with one Y being hydrogen, one Z being hydrogen and the other Y and Z being

where the R" groups are independently hydrocarbon groups having from 1 to 17 carbon atoms.

The above described esters are made by (1) reacting a 2,4-imidazolidinedione with a 1,3-diglycidyl-2,4-imidazolidinedione and (2) reacting the product of step (1) with a carboxylic acid. The 2,4-imidazolidinediones have the formula:

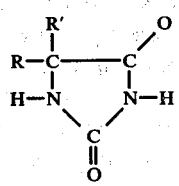

R and R' represent hydrogen groups, alkyl groups or when joined, a cycloalkyl group. (It should be understood that the R and R' groups can be the same or different.) Preferably R and R' are alkyl groups having from 1 to 5 carbon atoms. 2,4-Imidazolidinedione (commonly referred to as hydantoin) or a substituted 2,4-imidazolidinedione such as 5-methyl-2,4-imidazolidinedione, 5,5-dimethyl-2,4-imidazolidinedione, 5-methyl-5-ethyl-2,4-imidazolidinedione, 5-ethyl-5-amyl-2,4-imidazolidinedione, 5-propyl-2,4-imidazolidinedione, 5-isopropyl-2,4-imidazolidinedione and 5,5-pentamethylene-2,4-imidazolidinedione can be used in the first step.

The 1,3-diglycidyl-2,4-imidazolidinediones having the formula:

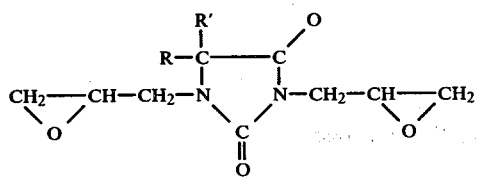

with R and R' as defined previously are commercially available or can be made by reaction of a 2,4-imidazolidinedione with an epihalohydrin, e.g., epichlorohydrin. Suitable catalysts for use in the reaction are tertiary amines such as triethylamine, tri-n-propylamine, benzyldimethylamine, N,N-dimethylaniline and triethanolamine, quaternary ammonium hydroxides, quaternary ammonium halides, alkali halides such as lithium chloride, potassium chloride and sodium chloride, and hydrazines with a tertiary nitrogen atom. As a general rule, the reaction of the imidazolidinedione or substituted imidazolidinedione with epihalohydrin occurs at elevated temperatures, e.g., from about 60° C. to about 200° C. Agents for splitting off hydrogen halide which are used are, as a rule, strong alkalis such as anhydrous sodium hydroxide or concentrated sodium hydroxide solution. However, other alkaline reagents such as potassium hydroxide, barium hydroxide, sodium carbonate or potassium carbonate can also be used.

The reaction of the imidazolidinedione and the diglycidyl imidazolidinedione occurs over a wide range of temperatures, i.e., from about 50° C. to about 200° C. The moles of each reactant is determinate of the final ester products of this invention. It is preferred that a molar ratio of the 2,4-imidazolidinedione or substituted 2,4-imidazolidinedione to the diglycidyl imidazolidinedione of from about 1:1.9 to about 1:2.2, most preferably about 1:2 be used.

Esters of the above described reaction product of step (1) are made by a subsequent reaction with a carboxylic acid. Such carboxylic acids can be saturated or unsaturated, aliphatic or cyclic compounds. The saturated carboxylic acids have from 2 to 18 carbon atoms. Cyclic carboxylic acids used in the reaction are aryl and alkylaryl compounds having from 7 to 11 carbon atoms, i.e., 6 to 10 carbon atoms exclusive of the carbon atom in the carboxyl group. Examples of such acids include acetic acid, propionic acid, butyric acid, caproic acid, myristic acid, palmitic acid, stearic acid, neodecanoic acid, dodecanoic acid, pelargonic acid, benzoic acid, toluic acid and phenylacetic acid. Unsaturated carboxylic acids can also be used, examples of which are myristoleic acid, palmitoleic acid, oleic acid, linoleic acid and linolenic acid. The monocarboxylic acids are preferred with the saturated monocarboxylic acids having from 8 to 18 carbon atoms being most preferred.

The formation of the ester occurs at a temperature of from about 50° C. to about 200° C. A suitable catalyst such as a tertiary amine, quaternary ammonium hydroxide, quaternary ammonium halide or lithium carbonate can be used.

The above-described esters have a relatively low molecular weight, yet are substantially non-volatile upon exposure to elevated temperatures. The esters can be thinned with a small amount of solvent to substantially reduce their viscosities. These properties make the esters especially useful in coating compositions where only a low level of organic solvent can be tolerated. Thus coating compositions can be formulated with the esters and suitable crosslinking agents using little or no organic solvent. The resultant compositions have a low viscosity and can be applied using conventional coating techniques. Moreover, coatings resulting from the compositions are durable, have a good appearance and can have a high gloss.

COATING COMPOSITIONS

Coating compositions of this invention consist essentially of from about 5 percent to about 90 percent of the above hydroxy-functional ester of substituted imidazolidinedione, preferably from about 10 percent to about 50 percent of the ester, and from about 5 percent to about 80 percent, preferably from about 20 percent to about 60 percent, of a suitable crosslinking agent. Examples of crosslinking agents are the aminoplasts, isocyanates, blocked isocyanates, phenoplasts and mixtures thereof. Preferred are the aminoplasts and blocked isocyanates. The aforedescribed classes of crosslinking agents are described in more detail in the following paragraphs.

Aminoplast resins are based on the addition products of formaldehyde with an amino- or amido-group carrying substance, e.g., urea, ethylene diurea, ethylene urea, melamine and benzoguanamine. Condensation products obtained from the reaction of alcohols and formaldehyde with melamine, urea or benzoguanamine are preferred herein. Useful alcohols used to make etherified products are monohydric alcohols such as methanol, ethanol, propanol, butanol, benzyl alcohol and butoxyethanol. An etherified melamine-formaldehyde resin is the preferred aminoplast resin. U.S. Pat. No. 4,075,141, Porter et al, Feb. 21, 1978 contains a description of aminoplast resins and is incorporated herein by reference.

Isocyanates useful as a crosslinking agent include any of the many organic isocyanates available. Examples include p-phenylene diisocyanate, biphenyl diisocyanate, toluene diisocyanate, 3,3'-dimethyl-4,4'-biphenylene diisocyanate, 1,4-tetramethylene diisocyanate, hexamethylene diisocyanate, 2,2,4-trimethylhexane-1,6-diisocyanate, methylene bis-(phenylisocyanate), isophorone diisocyanate, 1,2,4-benzene triisocyanate, polymethylene polyphenyl isocyanate, bis(isocyanatocyclohexyl) methane and methyl cyclohexyl diisocyanate, as well as derivatives thereof.

Blocked isocyanates containing substantially no free isocyanate groups and relatively inactive at room temperature are very useful crosslinking agents. Typical blocking agents are the phenols, thiols, oximes, caprolactams, and secondary aromatic amines. Many of these compounds are commercially available. "The Chemistry of Organic Film Formers", Robert E. Krieger Pub. Co., copyrighted 1977, by D. H. Solomon, pp 216–217, contains a description of many blocked isocyanates that can be used here. This disclosure is herein incorporated by reference.

Phenoplast resins include the condensation product of an aldehyde with a phenol. Formaldehyde is a preferred aldehyde. Various phenols can be used, e.g., phenol per se, cresol, para-phenylphenol, para-tertiarybutylphenol, para-tertiaryamylphenol and cyclopentylphenol. The methylol phenol ethers described in U.S. Pat. No. 2,597,330 (herein incorporated by reference) are especially useful.

The coating compositions consist essentially of the aforedescribed hydroxy-functional esters of substituted imidazolidinedione and the crosslinking agents. Generally, however, coating composition additives are included in the compositions. A solvent such as water or an organic solvent, e.g., the ketones, ethylene glycol monoalkyl ether acetates, the mono- and dialkyl ethers of ethylene and propylene glycol, xylene, toluene and lower alcohols can be used. The level of the organic solvent in the compositions, however, is less than about 40 percent, preferably less than about 30 percent, of the composition. Other coating composition additives include pigments, fillers, antioxidants, flow control agents, surfactants, catalysts and reactive diluents. Other curable resins can also be included in the coating compositions provided they do not represent more than about 60 percent of the composition.

The coating compositions are applied by any convenient method, including spraying, dipping and flow coating. The compositions have been found especially useful for the coating of metal substrates such as automotive parts.

The following examples are illustrative of the described invention. The exemplified process produces the hydroxy-functional ester of substituted imidazolidinedione of this invention.

EXAMPLE I

A five-liter reaction flask is set up with heating means, stirring means and a nitrogen sparge. The reaction flask is charged with 1693 grams of 5-ethyl-5-amyl-1,3-diglycidyl-2,4-imidazolidinedione (5.6 moles), available from the Ciba-Geigy Co. as LSU-609, 343 grams 5,5-dimethyl-2,4-imidazolidinedione (2.8 moles) and 4 grams ethyltriphenylphosphonium iodide. The mixture is heated to 100° C. and allowed to exotherm to 160° C. The mixture is held at the 160° C. for about 2 hours. Next, 964 grams of neodecanoic acid (5.6 moles) and 6 grams of dimethylcoco-amine are added and the temperature maintained at about 150° C. for about 2 hours until an acid number below 2 is obtained. The reaction mixture is then thinned with 328 grams of ethylene glycol monoethyl ether acetate.

The reaction mixture has a viscosity of Z-10, acid number of 0.6 and a hydroxyl number of 185.

EXAMPLE II

A coating composition is formulated as follows:

|  | Percent |
| --- | --- |
| Ester of Example I | 18.3 |
| Aminoplast resin (1) | 16.1 |
| Pigment paste (2) | 29.4 |
| Microgel dispersion (3) | 7.0 |
| Para-toluenesulfonic acid | 1.9 |
| Diisopropanolamine | 0.2 |
| Methyl ethyl ketone | 27.1 |

(1) The aminoplast resin is a methylated melamine-formaldehyde resin available from the American Cyanamid Co. as Cymel 303.
(2) The pigment paste contains 67 percent pigment, 12 percent grinding resin and 21 percent solvent.
(3) The microgel dispersion corresponds to the dispersion described in Example II of commonly assigned, copending application Serial No. 805,679, filed June 13, 1977.

The above composition is applied by spraying metal panels in an amount sufficient to provide a dry film thickness of about 2 mils. The panels are baked at 120° C. for 30 minutes to cure the composition. The coated panels have a satisfactory appearance as well as having good sag resistance, acid resistance, solvent resistance and water resistance.

The above examples illustrate the process of making the hydroxy-functional esters of substituted imidazolidinediones and their use in coating compositions.

What is claimed is:

1. A hydroxy-functional ester of a substituted imidazolidinedione having the formula:

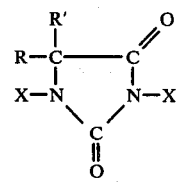

where X is hydrogen,

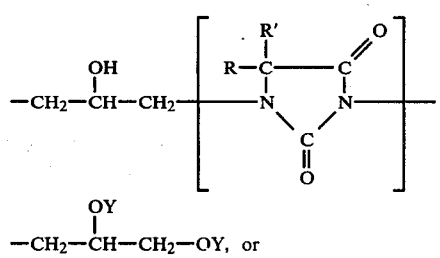

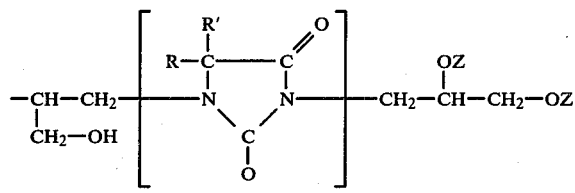

provided both X's are not hydrogen, with R and R' being independently hydrogen or hydrocarbon groups having 1 to 8 carbon atoms, with one Y being hydrogen, one Z being hydrogen and the other Y and Z being

where the R" groups are independently hydrocarbon groups having from 1 to 17 carbon atoms.

2. The ester of claim 1 wherein R and R' are hydrogens.

3. The ester of claim 1 wherein R and R' are alkyl groups.

4. The ester of claim 3 wherein the alkyl groups have from 1 to 5 carbon atoms.

5. The ester of claim 4 wherein R and R' are joined to form a cycloalkyl group.

6. The ester of claim 1 wherein R is hydrogen and R' is an alkyl group.

7. The ester of claims 2, 3 or 6 wherein the R" groups are alkyl groups.

8. The ester of claim 7 wherein the R" alkyl groups have from 7 to 17 carbon atoms.

9. The ester of claims 2, 3 or 6 wherein the R" groups are alkenyl groups.

10. The ester of claims 2, 3 or 6 wherein the R" groups are aryl or alkylaryl groups having from 6 to 10 carbon atoms.

11. The ester of claims 2, 3 or 6 wherein neither X is hydrogen.

12. A process for making a hydroxy-functional ester of a substituted imidazolidinedione comprising the steps of (a) reacting a 1,3-diglycidyl-2,4-imidazolidinedione having the formula:

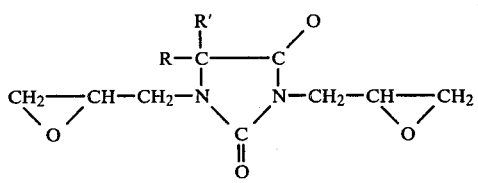

wherein R and R' are independently hydrogen or hydrocarbon groups having from 1 to 8 carbon atoms with a 2,4-imidazolidinedione of the formula:

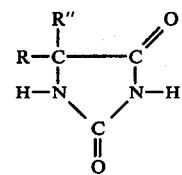

wherein R and R' are as defined previously; and (b) reacting the compound of step (a) with a carboxylic acid having from 2 to 18 carbon atoms to obtain the ester having the formula:

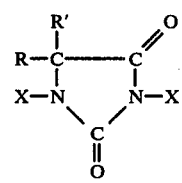

where X is hydrogen,

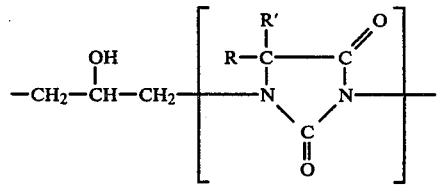

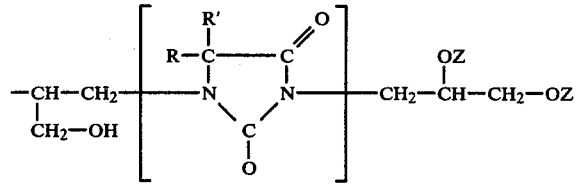

provided both X's are not hydrogen, where R and R' are independently hydrogen or hydrocarbon groups having 1 to 8 carbon atoms, with one Y being hydrogen, one Z being hydrogen and the other Y and Z being

where the R" groups are independently hydrocarbon groups having from 1 to 17 carbon atoms.

13. The process of claim 12 wherein R and R' are hydrogens.

14. The process of claim 12 wherein R and R' are alkyl groups.

15. The process of claim 14 wherein the R and R' alkyl groups have from 1 to 5 carbon atoms.

16. The process of claim 15 wherein the R and R' groups are joined together to form a cycloalkyl group.

17. The process of claim 12 wherein R is hydrogen and R' is an alkyl group.

18. The process of claims 13, 14 or 17 wherein the R" groups are alkyl groups having from 7 to 17 carbon atoms.

19. The process of claim 18 wherein neither X is hydrogen.

20. A coating composition containing less than about 40 percent organic solvent, consisting essentially of (a) from about 5 percent to about 90 percent of a hydroxy-functional ester of a substituted imidazolidinedione of the formula:

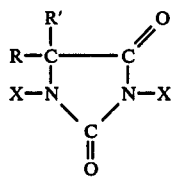

where X is hydrogen,

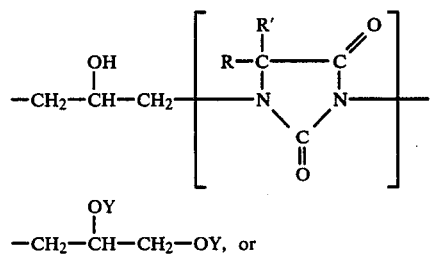

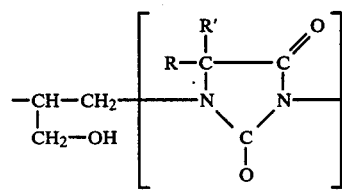

provided both X's are not hydrogen, where R and R' are independently hydrogen or hydrocarbon groups having 1 to 8 carbon atoms, with one Y being hydrogen, one Z being hydrogen and the other Y and Z being $$-\overset{O}{\underset{\|}{C}}-R''$$

where the R'' groups are independently hydrocarbon groups having from 1 to 17 carbon atoms; and (b) from about 5 percent to about 80 percent of a crosslinking agent selected from the group consisting of aminoplasts, isocyanates, blocked isocyanates, phenoplasts, and mixtures thereof.

21. The coating composition of claim 20 wherein R and R' are hydrogens.

22. The coating composition of claim 20 wherein R and R' are alkyl groups.

23. The coating composition of claim 22 wherein the alkyl groups have from 1 to 5 carbon atoms.

24. The coating composition of claim 23 wherein R and R' are joined to form a cycloalkyl group.

25. The coating composition of claim 20 wherein R is hydrogen and R' is an alkyl group.

26. The coating composition of claims 21, 22 or 25 wherein the R'' groups are alkyl groups.

27. The coating composition of claim 26 wherein the R'' alkyl groups have from 7 to 17 carbon atoms.

28. The coating composition of claims 21, 22 or 25 wherein the R'' groups are alkenyl groups.

29. The coating composition of claims 21, 22 or 25 wherein the R'' groups are aryl or alkylaryl groups having from 6 to 10 carbon atoms.

30. The coating composition of claims 21, 22 or 25 wherein neither X is hydrogen.

31. The coating composition of claim 30 wherein the crosslinking agent is an aminoplast.

32. The coating composition of claim 30 wherein the crosslinking agent is a blocked isocyanate.

33. The coating composition of claim 31 wherein the level of organic solvent in the composition is less than about 30 percent.

34. The coating composition of claim 33 wherein the composition consists essentially of from about 10 percent to about 50 percent of the ester and from about 20 percent to about 60 percent of the crosslinking agent.

* * * * *